(12) United States Patent
Blizzard et al.

(10) Patent No.: US 9,902,744 B2
(45) Date of Patent: Feb. 27, 2018

(54) HIGHLY DISPERSIBLE ANTIMICROBIAL AND ADHESION AGENTS

(71) Applicants: John D. Blizzard, Bay City, MI (US); Robert L. McKellar, Midland, MI (US)

(72) Inventors: John D. Blizzard, Bay City, MI (US); Robert L. McKellar, Midland, MI (US)

( * ) Notice: Subject to any disclaimer, the term of this patent is extended or adjusted under 35 U.S.C. 154(b) by 0 days.

(21) Appl. No.: 15/082,026

(22) Filed: Mar. 28, 2016

(65) Prior Publication Data

US 2017/0275304 A1   Sep. 28, 2017

(51) Int. Cl.
*C07F 7/08* (2006.01)
*A01N 55/00* (2006.01)

(52) U.S. Cl.
CPC ............ *C07F 7/0838* (2013.01); *A01N 55/00* (2013.01)

(58) Field of Classification Search
CPC .......... C07F 7/18; C07F 7/0838; A01N 55/00; A01N 55/02
USPC .................. 514/63; 424/405; 528/34, 38
See application file for complete search history.

(56) References Cited

PUBLICATIONS

Theuretzbacher et al. Current Opinion in Pharmacology, 2011, 11: 429-432.*
Bassetti et al. Annals of Clinical Microbiology and Antimicrobials 2013, 12:22, pp. 1-15.*
Shaffer R. K. Yale Journal of Biology and Medicine 86 (2013), pp. 261-270.*
Kint et al. Trends in Microbiology, Dec. 2012, vol. 20, No. 12, 577-585.*
Becker D.E. Anesth Prog 60:111-123, 2013.7.*

* cited by examiner

*Primary Examiner* — Venkataraman Balasubramanian

(57) ABSTRACT

Compositions of matter that have antimicrobial properties and adhesion properties and are highly dispersible in aqueous solutions. The presence of a large number of silanols on the molecules of this invention creates a solubility or dispersability of these molecules in aqueous solutions that is not obtainable from prior art antimicrobial monomers.

5 Claims, No Drawings

HIGHLY DISPERSIBLE ANTIMICROBIAL AND ADHESION AGENTS

BACKGROUND OF THE INVENTION

This invention deals with compositions of matter that have antimicrobial properties and adhesion properties and are highly dispersible in aqueous solutions. The presence of a large number of silanols on the molecules of this invention creates a solubility or dispersability of these molecules in aqueous solutions that is not obtainable from prior art antimicrobial monomers. The inventors herein are not aware of any like molecules in the prior art.

THE INVENTION

Thus, what is disclosed and claimed herein is a composition of matter having the average general formula:

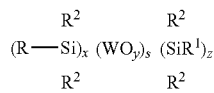

wherein the average molar ratio of x:y:z is 0.25-3:4:0.25-3, with the proviso that there is present at least one RSi— unit and at least one R'Si unit and W is independently selected from the group consisting essentially of Si, Ti, and Zr, and Al, wherein R is a core functionality based on the chemistry selected from the group consisting of glycidoxy, amino, acrylamide, methacrylamide, acrylate, methacrylate, $C_2$-$C_8$ alkenyl, mercapto, ester, isocyanato, epoxycyclohexyl, carboxylic acid, and

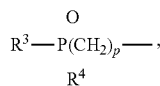

wherein p has a value of from 1 to 6 and $R^3$ is selected from the group consisting of hydroxyl and alkoxy groups having 1 to 4 carbon atoms.

$R^2$ is independently selected from the group consisting of hydroxyl groups,

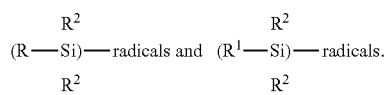

s has a value of about 1 to 5 and y has a value of 4 wherein $R^1$ is selected from the group consisting of:
i. a sulfonium salt of the formula $Si(R^5)_2C_dH_{2d}S^+(R^4)_2X^-$ in which $R^4$ is independently an alkyl group or aralkyl group wherein there is a total of less than 60 carbon atoms in the molecule, $R^5$ is independently selected from the group consisting of hydroxyl groups,

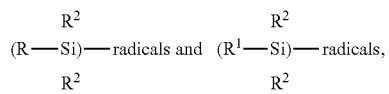

d is an integer of 1 or greater and $X^-$ is a water soluble monovalent anion;
ii. an isothiuronium salt of the formula $Si(R^5)_2C_dH_{2d}S^+C(NH_2)_2X^-$, wherein $R^5$ is independently selected from the group consisting of hydroxyl groups,

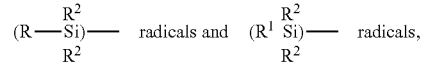

d is an integer of 1 or greater and $X^-$ is a water soluble monovalent anion;
iii. a phosphonium salt of the formula $Si(R^5)_2C_dH_{2d}P^+(R^6)_3X^-$ in which $R^6$ is independently selected from an alkyl group or aralkyl group wherein there is a total of less than 60 carbon atoms in the molecule, $R^5$ is independently selected from the group consisting of hydroxyl groups,

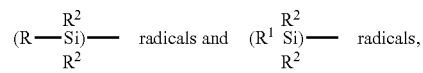

d is an integer of 1 or greater a $X^-$ is a water soluble monovalent anion and,
iv. an amine of the formula $Si(R^5)_2C_dH_{2d}N(H)(C_dH_{2d})NH_2$ wherein $R^5$ is independently selected from the group consisting of hydroxyl groups,

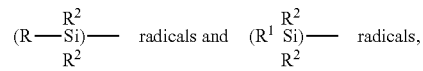

in which d is an integer of 1 or greater, wherein ($WO_y$) is derived from $W(OR^7)_4$ wherein ($OR^7$) is independently selected from the group consisting of
i. —$OCH_3$,
ii. —$OCH_2CH_3$,
iii. —$OCH(CH_3)_2$,
iv. —$O(CH_2)_3CH_3$,
v. —$OCH_2CH(CH_3)_2$,
vi. —O(2-ethylhexyl),
vii. acetoxy, and,
viii. oximo.

DETAILED DESCRIPTION OF THE INVENTION

One method for providing the materials of this invention comprises providing the components:

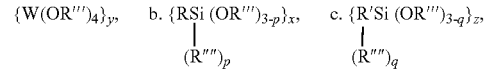

wherein the molar ratio of x:y:z is 0.25-3:4:0.25-3, $p$ and $q$ each independently have a value of 2 or less, and cohydrolyzing the components in the presence of a stoichiometric amount of water, and a catalyst for hydrolysis and condensation.

By careful, controlled hydrolysis of the precursor monomers, one can obtain these materials at very low molecular weights providing a large number of silanols on the molecules, the detail of which can be found infra in the specification, and in the examples.

The materials have the average general formula

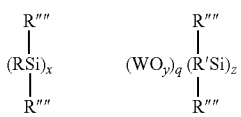

which is derived by the hydrolysis of the silane precursors

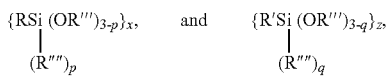

in conjunction with the orthosilicate, or orthotitanate, orthozirconate, or orthoaluminate, having the general formula

wherein the molar ratio of x:y:z is 0.25-3:4:0.25-3.

This hydrolysis is carried out using a stoichiometric or near stoichiometric amounts of water and a catalyst for hydrolysis and condensation. Stoichiometric amounts of water, or, an amount of water greater than stoichiometric, results in low molecular weight materials, which is one of the objectives of the method in this invention. Caution should be noted for the use of substantially lesser amounts of water as that will result in a residual amount of alkoxy in the material which is undesirable for purposes of this invention.

It is believed by the inventors herein that the key to this invention is the use of the molecule $(W(OR''')_4)_y$ as the third component of this invention. W in the case of this invention is independently selected from the group consisting of Si, Ti, Zr, and Al. Preferred for this invention is Si and Ti and most preferred is Si.

The (OR''') group is selected from the group consisting of —OCH$_3$, —OCH$_2$CH$_3$, —OCH(CH$_3$)$_2$, —O(CH$_2$)$_2$ CH$_3$, —OCH$_2$CH(CH$_3$)$_2$, —O(2-ethylhexyl), acetoxy, and, oximo. Preferred for this invention are the groups —OCH$_3$, —OCH$_2$CH$_3$, and —OCH(CH$_3$)$_2$, and most preferred are the —OCH$_3$ and —OCH$_2$CH$_3$ groups. Preferred orthosilicates and orthotitanates for this invention are Si(OCH$_2$CH$_3$)$_4$ and Ti(—OCH(CH$_3$)$_2$)$_4$.

Stoichiometry is based on the number of hydrolysable groups on the combined components. The reaction is carried out in the presence of base or acid, with acid being the preferred catalyst. The acid catalysts are preferred to be HCl, phosphoric, and acetic acids, with HCl and phosphoric acids being most preferred.

Bases that are useable herein are amines, NaOH, KOH and the like and preferred for this invention is NaOH. The hydrolysis reaction is carried out by combining the components in a predetermined ratio and then adding acidic or basic water to the components at a controlled rate to form silanols from the alkoxy moieties. For some end use applications of the inventive materials, a slightly higher molecular weight (higher number of silanol reactive groups) is preferred and in this case, the silicate component is treated for a short period of time by acidic or basic water to cause the silicate component to hydrolyze and condense before the other components are added By the preferred means, the following reaction sequence is achieved:

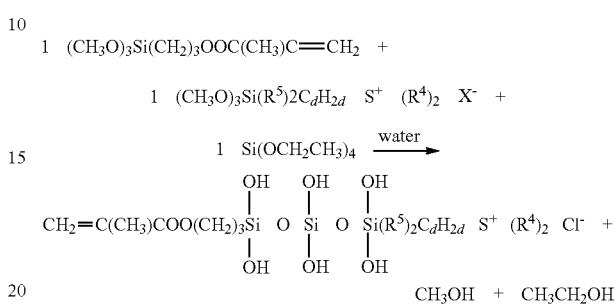

No heat is used in this reaction as higher temperatures (in excess of about 150° C.) may result in gelation of the reaction mixture. There is a small exotherm from the hydrolysis reaction but the heat is not sufficient to provide problems with the resultant product. No solvents are required in this reaction, but it is within the scope of this invention to utilize solvents. It should be noted that the byproduct of the hydrolysis reaction is alcohol. Typically, the products of this reaction do not need filtration.

As mentioned Supra, it is possible to enhance the molecular weight and thereby increase the amount of silanol functionality on the molecule by first mildly hydrolyzing the ortho precursor and then adding the remainder of the components.

Thus, a molecule having the following average formula may be obtained:

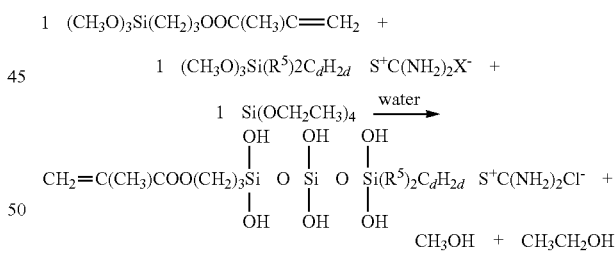

One can also provide a material having the formula:

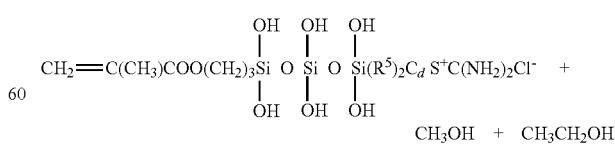

by hydrolyzing the components $(CH_3O)_3Si(CH_2)_3OOC(CH_3)C=CH_2$, 1 $Si(OCH_2CH_3)_4$ and 2 $(CH_3O)_3Si(R^5)_2C_dH_{2d}P^+(R^6)_3Cl^-$.

A preferred material is

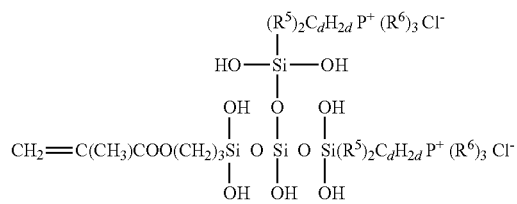

The materials are liquids as prepared. In some cases, if preferred, the by-produced alcohols and any residual water can be removed to provide a solid material, and in some cases the solid material is hard and appears to be almost crystalline and in some cases, the material is waxy or paste-like.

These compositions of matter have antimicrobial properties and adhesion properties and are highly dispersible in aqueous solutions. The presence of a large number of silanols on the molecules of this invention creates a solubility or dispersability of these molecules in aqueous solutions that is not obtainable from prior art antimicrobial monomers. The materials of this invention are also suitable for providing adhesion in combination with ionomers, especially glass ionomers.

EXAMPLES

| TEOS | | Tetraethylorthosilicate |
|---|---|---|
| Z-6070 | MTM | methyltrimethoxysilane |
| Z-6030 | MAPTMS | methacryloxypropyltrimethoxysilane |
| 8405 | | N-(trimethoxysilylpropyl) isothiuronium chloride |
| 2417 | | 2-(4-chlorosulfonylphenyl) ethyltrimethoxysilane |

The tetraethylorthosilicate or tetrabutyltitanate were placed in a 40 ml vial with a magnetic stirring bar. The functional trialkoxy-silane was added and allowed to mix for 30 minutes. Water, adjusted with KOH to pH 10 or HCl to pH 2, was added dropwise with agitation. This was allowed to hydrolyze for 60 minutes and 24 hours after which the solution was evaluated for appearance. All weights are in grams. Compound molecular weights were used to calculate the moles and molar ratios of each component.

TABLE 1

| | | Sample # | | | | | | |
|---|---|---|---|---|---|---|---|---|
| | Mw | 1 | 2 | 3 | 4 | 5 | 6 | 7 |
| Z-6030 | 248 | | | | | 2.48 | 2.48 | 2.48 |
| Z-6070 | 136 | 1.36 | 1.36 | 1.36 | | | | |
| TEOS | 208 | 2.08 | 2.08 | 6.24 | 2.08 | 2.08 | 2.08 | 6.24 |
| 8405 @ 50% in water | 274.8 | 5.5 (2.75) | 5.5 (2.75) | 5.5 (2.75) | 22 (11) | 2.75 | 5.5 | 2.75 |
| water pH = 10 | 18 | | 1.8 | | | 1.8 | 1.8 | 1.8 |
| Moles-6070/TEOS/8405 | | 1/1/2 | 1/1/2 | 1/3/1 | 0/1/4 | | | |
| Moles-6030/TEOS/8405 | | | | | | 1/1/1 | 1/1/2 | 1/3/1 |
| Solution @ 24 hours | | soft gel | OK | clear OK | clear OK | OK | OK | OK |
| Application, microbial kill | | 99.99 | | | | | | |

TABLE 2

| | | Sample # | | | | | | |
|---|---|---|---|---|---|---|---|---|
| | | 8 | 9 | 10 | 11 | 12 | 13 | 14 |
| Z-6030 | 248 | | | | | 2.48 | 2.48 | 2.48 |
| Z-6070 | 136 | 1.36 | 1.36 | 1.36 | | | | |
| TEOS | 208 | 2.08 | 2.08 | 6.24 | 2.08 | 2.08 | 2.08 | 6.24 |
| 2417 @ 50% in MeCl | 324.85 | 6.5 (3.25) | 6.5 (3.25) | 6.5 (3.25) | 26 (13) | 3.25 | 6.5 | 3.25 |
| water pH = 10 | 18 | 1 | 1.8 | 1.8 | 1.8 | 1.8 | 1.8 | 1.8 |
| Moles-6070/TEOS/2417 | | 1/1/1 | 1/1/1 | 1/3/1 | 0/1/4 | | | |
| Moles-6030/TEOS/2417 | | | | | | 1/1/1 | 1/1/2 | 1/3/1 |
| Solution @ 24 hours | | 2 phase miscible | OK | OK | OK | OK | OK | OK |
| Application, microbial kill | | 99.99 | | | | | | |

Purpose:

The purpose of this study was to evaluate the effectiveness of test materials labeled #1 and #8, in killing or reducing *Escherichia coli* (*E. coli*). The standard pour plate count test method was used to evaluate Percent Reduction of Colony Forming Units (CFU).

Study Design

The *E. coli* (lot number 168756) was purchased from Quanti-Cult™ and is derived from original ATCC® stock cultures. They are received dehydrated. A viable streak plate was colonized from this culture. One colony was transferred to 5 ml of sterile Tryptic Soy Broth (lot #A3303) and incubated overnight.

Antimicrobial activity is determined by comparing results from the test sample to simultaneously run controls or from the $T_0$. The concentration of the suspension is determined using serial dilution and plate counts to determine the amount of Colony Forming Units (CFU's)/ml of suspension.

The materials tested in this study are described in the Purpose section of this report. Sterile 0.3 mM $KH_2PO_4$ buffer was inoculated to a concentration of ~1.0-3.0×10$^5$ CFU/ml. A $T_0$ plate originated from the inoculated buffer for quantification and prepared 1:100 dilution to insure that viable inoculum was applied in the test system. The test materials were formulated in 20×150 ml test tubes. Aliquots of 0.3 grams of each of the materials (#1 and #8) were added to sterile test tubes. Five ml of Tryptic Soy Broth was added to each tube and the tubes inoculated with 1×10$^5$ CFU, *E. coli*. The materials were incubated for 48 hours. $T_0$ of the inoculums was 9.6×10$^4$ CFU/ml. One milliliter aliquots of the test article inoculums were added to Petri dishes, Plate Count Agar added and swirled and the plates were incubated at 35° C. overnight.

Results

The results show 16 CFU/ml for material #1 or >99.9% reduction and material #8 had 0 CFU/ml (no growth) or 100% reduction.

What is claimed is:

1. A composition of matter having the average general formula:

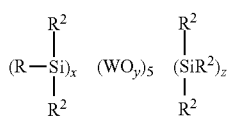

wherein the average molar ratio of x:y:z is 0.25-3:4:0.25-3, with the proviso that there is present at least one RSi— unit and at least one —R$^1$═—Si— unit and W is independently selected from the group consisting essentially of Si, Ti, and Zr, and Al, wherein R is a cure functionality based on the chemistry selected from the group consisting of glycidoxy, amino, acrylamide, methacrylamide, acrylate, methacrylate, $C_2$-$C_8$ alkenyl, mercapto, ester, isocyanato, epoxycyclohexyl, carboxylic acid, and

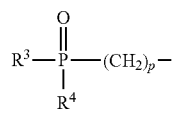

wherein p has a value of from 1 to 6 and R$^3$ is selected from the group consisting of hydroxyl and alkoxy groups having 1 to 4 carbon atoms;

R$^2$ is independently selected from the group consisting of hydroxyl groups,

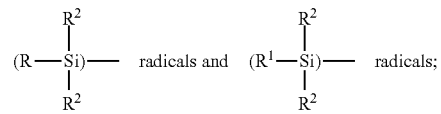

s has a value of about 1 to 5;
y has a value of 4;
R$^1$ is selected from the group consisting of:
  i. a sulfonium salt of the formula
  $Si(R^5)_2C_dH_{2d}S^+(R^4)_2X^-$ in which R$^4$ is independently an alkyl group or aralkyl group wherein there is a total of less than 60 carbon atoms in the molecule, R$^5$ is independently selected from the group consisting of hydroxyl groups,

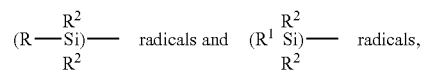

d is an integer of 1 or greater and X$^-$ is a water soluble monovalent anion;
  ii. an isothiuronium salt of the formula
  $Si(R^5)_2C_dH_{2d}S^+C(NH_2)_2X^-$, R$^5$ is independently selected from the group consisting of hydroxyl groups,

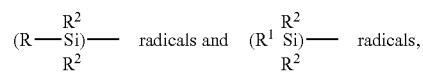

d is an integer of 1 or greater and X$^-$ is a water soluble monovalent anion;
  iii. a phosphonium salt of the formula
  $Si(R^5)_2C_dH_{2d}P^+(R^6)_3X^-$ in which R$^6$ is independently selected from an alkyl group or aralkyl group wherein there is a total of less than 60 carbon atoms in the molecule, R$^5$ is independently selected from the group consisting of hydroxyl groups,

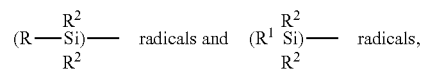

d is an integer of 1 or greater and X$^-$ is a water soluble monovalent anion and,
  iv. an amine of the formula
  $Si(R^5)_2C_dH_{d2}N(H)(C_dH_{2d})NH_2$ wherein R$^3$ is independently selected from the group consisting of hydroxyl groups,

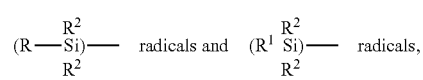

in which d is an integer of 1 or greater, wherein (WO$_y$) is derived from W(OR$^7$)$_4$ wherein (OR$^7$) is independently selected from the group consisting of
  i. —OCH$_3$,
  ii. —OCH$_2$CH$_3$,
  iii. —O CH(CH$_3$)$_2$,
  iv. —O(CH$_2$)$_3$CH$_3$,
  v. —OCH$_2$CH(CH$_3$)$_2$,
  vi. —O(2-ethylhexyl),
  vii. acetoxy, and,
  viii. oximo.

2. A composition of matter comprising a composition of claim 1 and an ionomer.

3. A composition as claimed in claim 1 in combination with a modified glass ionomer.

4. A method of providing adhesion, the method comprising providing a composition of claim 1 and combining said composition with an ionomer and thereafter applying said combination to a substrate.

5. The method as claimed in claim 4 wherein the ionomer is a glass ionomer.

\* \* \* \* \*